United States Patent

Stearns

[11] 4,158,630
[45] Jun. 19, 1979

[54] CHROMATOGRAPHIC MULTI-SAMPLE VALVING APPARATUS

[76] Inventor: Stanley D. Stearns, 7812 Bobbit, Houston, Tex. 77055

[21] Appl. No.: 881,164

[22] Filed: Feb. 24, 1978

[51] Int. Cl.$^2$ ............................................. B01D 15/08
[52] U.S. Cl. .................................... 210/198 C; 55/386
[58] Field of Search .......................... 210/31 C, 198 C; 55/197, 386; 137/625.13, 625.41; 222/168.5

[56] References Cited

U.S. PATENT DOCUMENTS

| 3,373,872 | 3/1968 | Hrdina | 210/31 C |
| 3,524,305 | 8/1970 | Ives | 55/386 |
| 3,862,038 | 1/1975 | Takeuchi et al. | 210/198 C |
| 4,042,499 | 8/1977 | Ramstar | 210/198 C |

Primary Examiner—John Adee
Attorney, Agent, or Firm—Donald Gunn

[57] ABSTRACT

Apparatus for delivering different samples to a liquid chromatograph is disclosed. The valving apparatus includes a commutated valve having N loops, where N is a whole number integer. The loops are isolated from one another. Selected loops are cycled by rotation of an inlet and outlet connected to selected loops. The valving apparatus further includes a valve mechanism having multiple ports which connect with an inlet, a sample holding loop, a liquid chromatographic pump, a chromatographic column for separation of constituents of the sample and other functional connections to carry on chromatographic analysis.

7 Claims, 2 Drawing Figures

CHROMATOGRAPHIC MULTI-SAMPLE VALVING APPARATUS

BACKGROUND OF THE DISCLOSURE

Liquid chromatographic analysis is an important procedure in chemical testing and analytical work. Liquid chromatographs do a very good job. Substantial labor is required, however, to deliver a large number of small specimens to a chromatograph.

This disclosure is directed to a multi-sample injection apparatus for a liquid chromatograph analyzer. The apparatus of the present invention is installed upstream of a liquid chromatograph to deliver multiple samples. In the analysis of a sample, it is necessary to deliver it to the chromatograph. Delivery of a sample to a chromatograph entails substantial hand labor. The hand labor can, perhaps, be ignored where only one or two samples must be tested. Quite often, a chromatograph is operated to test numerous different samples through the day. This means that the test personnel must operate the equipment many times during the day. With each injection, certain valves must be opened and closed in a set procedure to deliver a sample. The sample is then delivered to the chromatograph, and the test is run.

The foregoing procedure is disruptive and wasteful of test personnel time, energy and effort. More importantly, it fairly well ties test personnel to the chromatograph because they must come back, time and again, to the test equipment to inject the next sample to be tested by contrast, the present invention is an apparatus which enables test personnel to install all of the samples in the apparatus at one time. If, for instance, the test personnel has twelve specimens to be tested, all twelve can be loaded at one time. When all specimens have been loaded, the equipment can then be left untended. The samples are then delivered in sequence for individual tests.

In such a procedure, it is necessary to load the specimens as a group and yet maintain separation between individual specimens. It is not desirable that two specimens, delivered consecutively, run together. Chemical analysis of the mixed specimens would then be incorrect.

The present invention is able to deliver multiple specimens to be tested without slip up. In most valving installations installed on chromatographs, there is a correct sequence of valve operations. If an incorrect sequence is used, sample material can be lost. Sometimes, this is a catastrophic occurrence which cannot be permitted. The present invention is able to operate in a foolproof fashion so that there is no possibility of losing a specimen.

BRIEF SUMMARY OF THE APPARATUS

The apparatus of this disclosure is a valving system for delivery of samples to a liquid chromatograph. It is able to deliver multiple samples. Multiple samples are delivered by the apparatus by first loading various samples in storage loops. All of the storage loops are accessed by a commutated valve mechanism which selects first one and then another sample storage loop. Multiple loops can be used. The loops accommodate up to N specimens, where N is a whole number integer. The apparatus further includes a valve mechanism which connects the various components of the chromatographic system together, including an inlet port, a connection to a pump, connection with a liquid chromatograph column, a vent for spent specimens and so on.

DETAILED DESCRIPTION OF THE ILLUSTRATED EMBODIMENT

Figure 1:
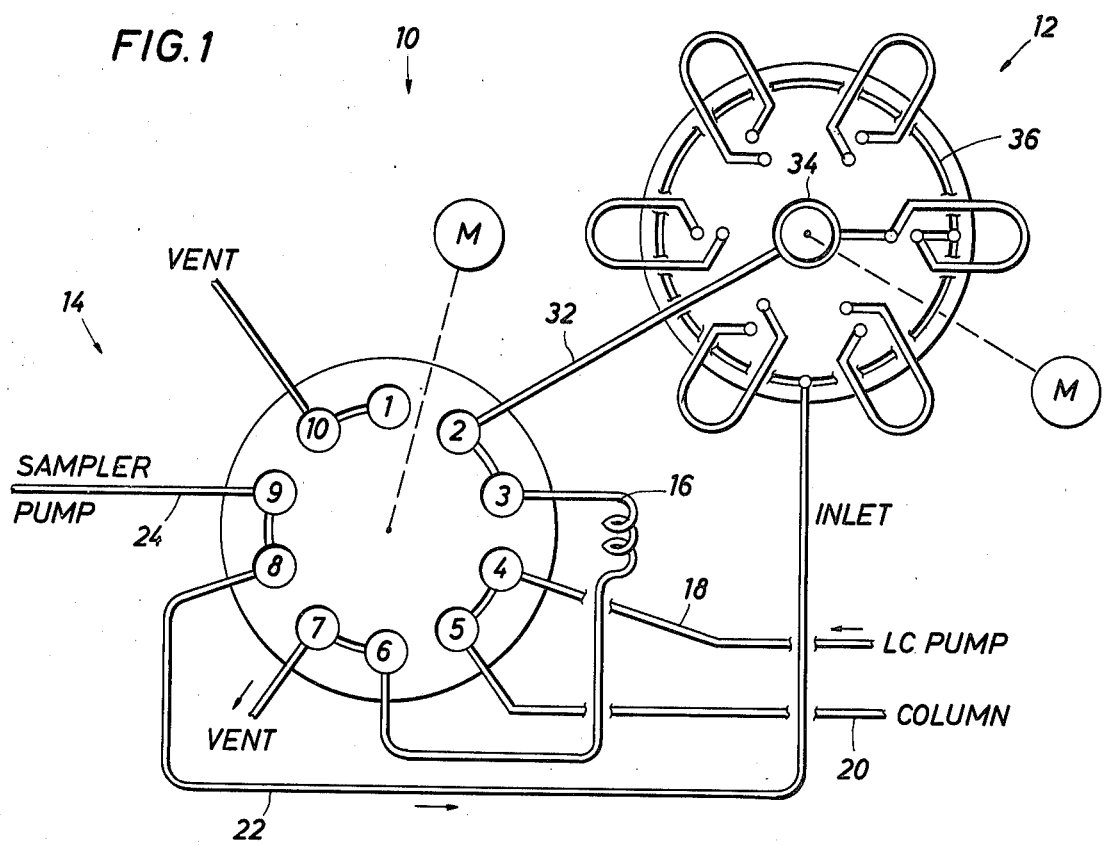
FIG. 1 is a schematic piping diagram of the valving apparatus of the present invention showing a set of connections by which N specimens can be stored in N storage loops and are delivered through a valving apparatus for sequential testing.

In the drawings, the numeral 10 identifies the valving apparatus of the present invention. It includes two major assemblies. The first major assembly is a sample loop valve apparatus identified generally at 12. The loop selector valve 12 enables up to N storage loops to receive up to N specimens. In this instance, N is a whole number integer. The numeral 14 identifies a valving apparatus. Both will be discussed in detail hereinafter.

The loop selector valve 12 will be described first. It incorporates a stator and rotor. It further includes two N ports for connection to N sample storage loops. Half of the ports are connected to an inlet manifold, and half of the ports are connected to an outlet manifold. The inlet and outlet manifolds are rotatable by rotating the apparatus so that inlet and outlet conduits connect to a selected isolated storage loop. Each loop is isolated from the adjacent loop. Each loop comprises an individually attached, small tube having a diameter and length calibrated to receive and store a specified quantity. The quantity can be quite small, or it can be quite large. if the tubing is fairly long, it is wrapped into several turns. Even though it is wrapped in several turns, the inlet and outlet are connected to the respective inlet and outlet ports provided for each loop.

The loop selector valve 12 incorporates a rotor which connects the inlet and outlet lines to a specified loop. When this occurs, the content of that particular loop is enabled for delivery.

Attention is next directed to the valve apparatus 14. It is a multi-port valve apparatus in the preferred embodiment. It incorporates a stator and rotor assembly, also. In the preferred embodiment, it incorporates ten ports. Internal porting switches between two sets of conditions. In the preferred and illustrated embodiment, the ten ports that are included are connected in the following combinations. The ports are connected in the following manner. FIG. 1 shows the first port connected to the last port. This is achieved in the first position of the rotor. The rotor preferably moves between stops to achieve the first position when moved to the extreme position permitted by rotation. Rotation in the opposite direction carries the rotor against the opposite stop at which time the first and second ports are connected together. The two sets of positions are identified in the chart listed below.

| Load Position (FIG. 1) | Operate Position |
| --- | --- |
| 10–1 | 1–2 |
| 2–3 | 3–4 |
| 4–5 | 5–6 |
| 6–7 | 7–8 |

| Load Position (FIG. 1) | Operate Position |
| --- | --- |
| 8-9 | 9-10 |

The preferred and illustrated porting system takes advantage of ten ports in a single body so that rotation of a single member synchronously achieves connections. This avoids undesired misconnections.

The external connections of the ten ports is of great interest. They will be described in numerical sequence.

The first port is a syringe injection entry port. A sample or specmen is injected through this port. A second port is connected to the valve 12. It is connected by a conduit 32 which connects to a first internal manifold 34 in the valve 12. The valve 12 additionally includes a second manifold 36.

The third port of the valve 14 is connected with a holding loop 16. The holding loop 16 additionally connects to the sixth port. The fourth port is connected to a conduit 18 which inputs a flow from the liquid chromatograph pump. Sometimes, these pressures are quite high to initiate proper operation of the chromatographic column. The fifth port is connected to a conduit 20 which then flows through the column.

The seventh port is an external vent passage to some suitable disposal device. The eighth port is connected through a conduit 22 to the manifold 36 in the loop storage valve 12. The ninth port is connected via a conduit 24 to the sampler pump which provides a suitable flow rate for transfer of the sample. The tenth port is connected to vent.

While the foregoing details many of the connections, the operation of the device is better understood by referring to a sequence of operation. Assume that the valve 12 includes a sample storage loop 28 which is empty. Assume that it includes another sample storage loop 30 which is also empty. For purposes of description, a sequence of operations will be set forth in which the loops are filled.

Figure 2:
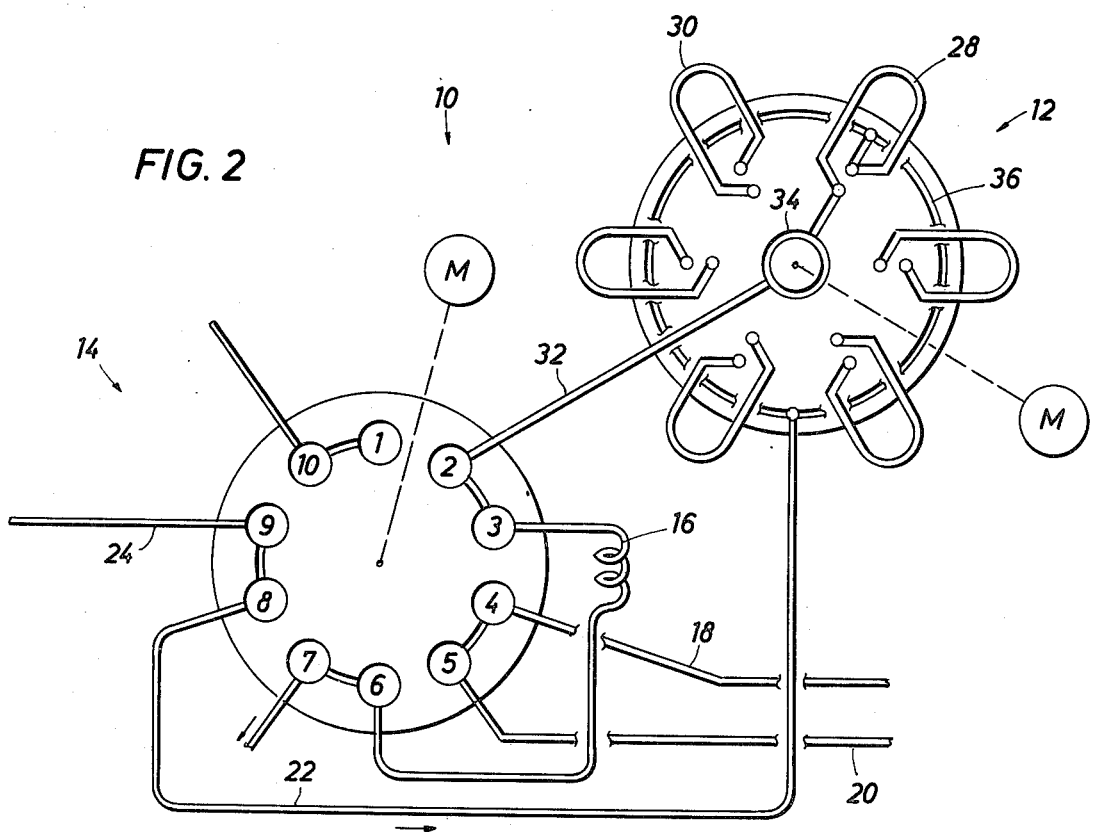
FIG. 2 is a view similr to FIG. 1 showing operation of the valving apparatus to achieve delivery of the specimens in the specimen holding loops.

Tracing through one cycle of operation, the fill or load sequence is as follows. Through the use of an injection syringe, a sample is introduced at the first port and flows to the second port. It flows from the second port through the conduit 32 to the manifold 34 and into the selected storage loop. It fills the storage loop. Any surplus flows through the conduit 22 to the eighth port, internally of the valve 14 to the seventh port and to the vent. This loading sequence is accomplished in relatively straightforward order. After the first sample has been loaded, the apparatus is prepared for loading the next sample. This is achieved by turning the rotor of the valve 12 to connect the manifolds 34 and 36 with a second loop. As an example, it can be rotated counterclockwise in FIG. 1 of the drawings to connect with the loop 28 as illustrated in FIG. 2.

The foregoing sequence describes how one sample or specimen is loaded into a single sample storage loop. After the first sample or specimen is loaded, the loop selector valve 12 is operated to load a second loop, such as the loop 28. A second sample or specmen is injected in the same sequence through the inlet port 1. This process is repeated until N sample loops are filled. On each injection, it may be necessary to utilize a clean syringe. It may further be necessary to utilize a suitable carrier between samples to provide sample isolation. In other words, the samples flow sequentially through the conduit 32, and it is desirable that they be isolated from one another to avoid comingling samples. Techniques for handling this problem are well known. Another precautionary factor is sizing the sample size to the sample loop. Standard sample loops can be obtained in various sizes, ranging from a fraction of a microliter to upwards of about 250 microliters. Larger loops are known and can also be used. In any case, the loop size is selected, and a suitable loop capacity is determined for a given storage loop.

After the several storage loops have been loaded with samples, the apparatus is prepared for delivery of a sample for testing.

Actual testing will be described next. For this, it is presumed that all the sample storage loops hold a single specimen in each. The valve 12 is operated to the first sample loop, and it is positioned so that the sample loop is connected with the conduits 22 and 32. The rotor of the valve 14 is operated to connect the port 2 with port 3. The sampler pump is operated to deliver a pressure surge through the conduit 24 input to the port 9 which is thereby transferred to the port 8, out through the conduit 22, through the commutated sample storage loop in the valve 12, then through the conduit 32 and input to the port 2, transferred by the rotor to port 3 and then output to the loop 16. The flow path continues from the loop 16 through the port 6 and then the port 7 to vent. A sufficient flow volume passes through this route to move the sample to the loop 16. Surplus is vented. The sample is held at that loop. When stored in this loop, it is isolated from the chromatograph. However, it is stored in the loop 16 preparatory to delivery to the chromatograph. The valve 14 is then operated to the other position whereby the ports 3 and 4 are joined together through the rotor, and the ports 5 and 6 are also joined together. This, then, describes a flow path under urging of a different pump, namely, the liquid chromatograph pump. This flow path includes the following sequence: pressure flow is delivered from the pump through the conduit 18, the input port 4, the port 3 and then flows outwardly into the storage or holding coil 16, thereafter flowing into the port 6 and out the port 5 through the conduit 20 to the chromatographic column. This delivers the sample of interest to the chromatograph for testing. While the apparatus is in this position, no high pressure is applied to the loop selector valve 12. It will be observed that the sampler pump connected through the conduit 24 is connected to vent through the port 10. This neutral state avoids disturbing samples in the various sample injection loops.

The next step is to rotate the loop selector valve 12 to the next sample of interest. This movement is achieved by simply rotating the rotor of the valve 12. When the position is achieved, the apparatus is then prepared for testing the next sample. However, the sample has to be delivered from the valve 12 back through the valve 14 and then to the storage loop 16. The valve 12 is prepared by moving to the sample loop of interest, and, thereafter, the valve 14 is operated. When it operates, the sequence described above for transfer of the sample from the selected storage loop to the loop 16 is repeated. Once at that location, the next operation can proceed whereby the sample is transferred from the loop 16 to the chromatographic column through the conduit 20.

This sequence can be repeated indefinitely.

Through the use of suitable motors which are indicated schematically in the drawings, the rotors of the valves 12 and 14 can be advanced. The valve 12 has as many operative positions as it has loops. Thus, it has N operative positions for N sample storage loops. The valve 14 has two operative positions for its rotor. Preferably, stops are used to limit travel. These positions have been described above.

Several practical things have been omitted. For instance, it is sometimes necessary to purge the system after the transfer of one sample so that it does not comingle with the next sample. Purging is achieved quite easily. For instance, the valve 14 is purged between samples. A purge material can be pumped through the route beginning with the sampler pump and the conduit 24 and emerging to vent at port 7.

The foregoing is directed to the preferred embodiment of the present invention. This embodiment preferably utilizes high quality stainless steel stator and inert polymeric rotor for each of the valves. They are drilled with ports or passages as shown schematically herein, and they are further connected in the manner described. The conduits, tubes and other passages including the members 18, 20, 22, 24 and 32 are preferably small diameter, high quality, tubular members. They are preferably rather short so that the specimens are not exposed to substantial travel.

Another practical factor to be observed in the use of the present invention is suitable pressure equalization so that the sample is not blown through the equipment by excess pressure. To this end, the sampler pump and the chromatograph pump are brought up to suitable pressure to obtain transfer and delivery of the specimen without precipitous results.

The apparatus can be used to hold two or more samples in a sample loop dependent on using a small diameter, nonwetting, capillary tube. Bubbles between samples provide sample isolation to enable two or more specimens to be placed in a single loop.

The foregoing describes the preferred embodiment, but the scope thereof is determined by the claims which follow.

I claim:

1. Sample injection apparatus for delivering a sequence of samples to a chromatographic detection apparatus which injection apparatus comprises:
   (a) loop selector valve means having a plurality of sample storage loops connected thereto and which further includes inlet and outlet means whereby individual samples can be stored in individual isolated storage loops connected thereto; and
   (b) chromatographic column valve means including an inlet port and flow path for introduction of a specimen of interest to be stored in a particular storage loop of said loop selector valve means, a second flow path selectively serially communicated with said selected storage loop and a chromatographic column, and a third flow path selectively opened and closed through said column valve means from a sampler pump to said loop selector valve means and selectively flowing to said column valve means through said selected sample holding loop to deliver a selected sample to a chromatographic column.

2. The apparatus of claim 1 wherein said loop selector valve means comprises N sample loops, and each of said sample loops is connected to two ports, and wherein the ports are grouped for connection into an inlet manifold and a separate outlet manifold and further including rotor means for commutating one of the loops to said manifolds.

3. The apparatus of claim 1 wherein said last named valve means incorporates at least nine ports, and wherein the ports provided therein include:
   (a) a sample injection port;
   (b) a second port serving as an outlet port connecting said valve means with said loop selector valve means;
   (c) third and fourth ports connected with a holding loop;
   (d) fifth and sixth port means adapted to be connected with the chromatograph pump and adapted to be connected to the chromatographic column;
   (e) a seventh port adapted to be connected as an inlet port with said loop selector valve means;
   (f) an eighth port adapted to be a sampler pump port adapted to be connected with a sampler pump; and
   (g) a ninth port adapted to be connected as a vent port.

4. The apparatus of claim 3 wherein said ports comprise ten in number and are switchable between a pair of valve positions, said valve means comprising a rotor switchable to achieve two valve positions and two combinations of connections by said ports.

5. The apparatus of claim 4 including a rotatable rotor in a stator operable between two positions to achieve switching as described above.

6. The apparatus of claim 1 including a single sample holding loop connected to a pair of ports on said column valve means.

7. The apparatus of claim 1 wherein said column valve means is a two position, ten port, single valve apparatus.

* * * * *